United States Patent [19]

Ratcliffe et al.

[11] 4,407,984
[45] Oct. 4, 1983

[54] DENTAL COMPOSITIONS

[75] Inventors: Maurice J. Ratcliffe; Thomas A. Roberts, both of Congleton, England

[73] Assignee: Imperial Chemical Industries PLC, London, England

[21] Appl. No.: 321,225

[22] Filed: Nov. 13, 1981

[30] Foreign Application Priority Data

Dec. 3, 1980 [GB] United Kingdom ............... 8038805
Jul. 9, 1981 [GB] United Kingdom ............... 8121235

[51] Int. Cl.³ ............................................. C08L 35/02
[52] U.S. Cl. ..................... 523/115; 523/116; 523/118; 524/140; 524/493; 433/228
[58] Field of Search ............. 523/115, 116, 117, 118, 523/120, 220; 433/168, 199, 212, 222, 228

[56] References Cited

U.S. PATENT DOCUMENTS

| | | |
|---|---|---|
| 3,663,501 | 5/1972 | Adams et al. ................... 523/116 |
| 3,792,531 | 2/1974 | Rossi . | 
| 3,835,090 | 9/1974 | Gander et al. ................... 523/116 |
| 3,845,009 | 10/1974 | Gander ........................... 523/116 |
| 3,926,906 | 12/1975 | Lee et al. ........................ 523/116 |
| 4,297,266 | 10/1981 | Ibsen et al. ..................... 523/115 |
| 4,302,376 | 11/1981 | Walkowiak et al. ............. 523/117 |

FOREIGN PATENT DOCUMENTS

| | | |
|---|---|---|
| 13491 | 7/1980 | European Pat. Off. . |
| 1401805 | 7/1975 | United Kingdom . |
| 1408265 | 10/1975 | United Kingdom . |
| 1488403 | 10/1977 | United Kingdom ............. 523/116 |
| 1493393 | 11/1977 | United Kingdom . |
| 1544776 | 4/1979 | United Kingdom . |

*Primary Examiner*—Lewis T. Jacobs
*Attorney, Agent, or Firm*—Cushman, Darby & Cushman

[57] ABSTRACT

A fluid dental composition which comprises a liquid ethylenically unsaturated polymerizable material and a polymerization catalyst therefor and a selected mixture of fine particle size and large particle size fillers and dispersing agent particularly for the former filler, the compositions having physical properties desirable as an amalgam potential replacement.

17 Claims, 2 Drawing Figures

Fig.1.

Fig.2.

DENTAL COMPOSITIONS

This invention relates to dental compositions comprising polymerisable material and inorganic fillers.

Many polymerisable materials have been used for dental applications. Examples of materials include polyurethanes, monomeric and polymeric acrylates and methacrylates, polyamides, epoxy-compounds, polystyrenes. Many applications have been envisaged such as fillings, crowns, denture base, coating, sealants and cements. In some of these applications it has been proposed to add inorganic fillers in order to confer desired pigmentation and/or strength.

Preferred polymerisable materials used in dental filling compositions include diacrylate such as the reaction product of Bisphenol A and glycidyl methacrylate, sometimes called bis-GMA as described in U.S. Pat. No. 3,066,112 and such as those described in German Offenlegungsschrift No. 2816823 and vinyl urethane prepolymer such as those described in British patent specification No. 1352063. These ethylenically unsaturated materials are polymerised in situ using a conventional redox (e.g. amine peroxide) catalyst system or ultra violet preferably visible light catalyst system such as that described in British patent specification No. 1408265. The composition may contain up to about 90% by weight of an inert inorganic filler as described in for example British patent specification Nos. 1465897, 1488403, 1498421, U.S. Pat. Nos. 3,629,187 and 3,709,866, and German Offenlegungsschrift No. 2419887.

There has been a requirement for a considerable time for a polymerisable material-based composite which when cured has physical properties particularly wear and tensile properties similar to or better than amalgam.

It has now been found that inclusion of a mixture of inorganic fillers having certain selected range of particle size and concentration in the composition provides for example a dental composite having such a desirable compromise of physical and aesthetic characteristics.

According to the present invention a fluid dental composition is provided which comprises:
(a) liquid polymerisable material (A)
(b) a mixture of fillers (B) in volume fraction from 60% to 85% where volume fraction is expressed as $$\left(\frac{\text{volume } B \times 100}{\text{volume } A + \text{volume } B}\right)$$

said mixture of fillers comprising fine particle size filler and large particle size filler, the fine particle size filler having a means size value in the longest direction of less than 0.5 μm and being present in volume fraction from 10% to 55% where volume fraction is expressed as

$$\left(\frac{\text{volume fine} \times 100}{\text{volume } A + \text{volume fine}}\right),$$

and the large particle size filler having mean size value in the longest dimension of 0.5 μm to 80 μm,
(c) polymerisation catalyst for the liquid polymerisable material, and
(d) dispersing agent.

By the term fluid is meant a range of viscosity for example sufficiently stiff at ambient temperature to enable the composition used as a filling material to be applied to a tooth cavity in a coherent mass but not having so low a viscosity that the composition flows readily from the tooth cavity and for example when used as a glaze a viscosity sufficient for flow over a tooth surface. By the term liquid, applied to the polymerisable material is meant such viscosity at ambient temperature as will make, with any other liquid additives, e.g. (c) and (d), the composition fluid without the polymerisable material having undue volatility.

The polymerisable material may be any liquid ethylenically unsaturated polymerisable resin suitable for dental applications. Preferably the material is a diacrylate or dimethacrylate. Typical of such materials are those hereinbefore described. Most preferred materials are vinyl urethanes such as for example those described in British patent specification Nos. 1352063, 1465897, 1498421 and German Offenlegungsschrift No. 2419887 or the reaction product of a diol such as a glycol but particularly a bisphenol with a glycidyl alkacrylate such as those described for example in U.S. Pat. Nos. 3,066,112, and 4,131,729 (the disclosures in these specifications are incorporated herein by way of reference).

A preferred reaction product of a glycidyl alkacrylate and a diol has the formula:

Preferred vinyl urethanes described in the aforesaid British patent specification and German offenlegungsschrift are the reaction product of a urethane prepolymer and an ester of acrylic or methacrylic acid with a hydroxy alkanol of at least 2 carbon atoms, the urethane prepolymer being the reaction product of a diisocyanate of the structure $OCN-R^1-NCO$ and a diol of the structure $HO-R^2-OH$ wherein $R^1$ is a divalent hydrocarbyl group and $R_2$ is the residue of a condensate of an alkylene oxide with an organic compound containing two phenolic or alcoholic groups.

Other suitable vinyl urethanes include those made by the reaction of alkyl and aryl, preferably alkyl, diisocyanates with hydroxy alkyl acrylates and alkacrylates such as those described in British patent specification Nos. 1401805, 1428672 and 1430303 (the disclosure of which are included herein by way of reference), vinyl maleate urethanes and vinyl isocyanurates.

The polymerisable material may be a solid or semi-solid and as the siliceous material is also solid it is often necessary (in order to produce a composition which is fluid) to add to the composition sufficient copolymerisable liquid ethylenically unsaturated monomer to make the composition fluid, and in particular to give the composition a cohesive paste-like consistency without being too runny. If desired, the composition may include liquid copolymerisable ethylenically unsaturated monomer even where all the polymerisable components are liquid. The term liquid polymerisable material includes a mixture of such solid or semi-solid with liquid copolymerisable monomer.

Hence the dental composition may contain a mixture of liquid copolymerisable ethylenically unsaturated monomers and should contain such a liquid monomer when the other monomer is a solid in order that the dental filling composition be fluid and in particular have a paste-like consistency.

The amount of such ethylenically unsaturated monomer used may desirably be just sufficient to achieve the desired fluidity in the dental filling composition. It is preferred to use in the present composition between 25% and 150% of ethylenically unsaturated monomer by weight of polymerisable prepolymer.

Suitable liquid copolymerisable ethylenically unsaturated monomers, the polymers of which should be water insoluble, include vinyl monomers, e.g. vinyl esters such as n-hexyl, cyclohexyl and tetrahydrofurfuryl acrylates and methacrylates. The monomers should be non-toxic.

Polyfunctional vinyl monomers, that is, monomers containing two or more vinyl groups are also suitable. Suitable monomers include, for example, glycol dimethacrylates, diallyl phthalate and triallyl cyanurate. Indeed such monomers may if they possess exceptionally low volatility and odour be used as the only polymerisable material in the present composition.

The compositions of the present invention contain filler in volume fraction (V fill) from 60% to 85%, preferably 60% to 75% where $$V\,\text{fill} = \frac{F}{P + F} \times 100$$

in which F is the total volume of filler and P is the volume of polymerisable material.

The filler comprises a mixture of fine particle size filler and large particle size filler. The fine particle size filler (FF) is present in the composition in volume fraction ($V_{FF}$) from 10% to 55%, most preferably 10% to 25% where $$V_{FF} = \frac{\text{volume } FF \times 100}{P + \text{volume } FF}$$

By fine particle size filler is meant a filler having a mean size value in the longest dimension of less than 0.05 μm, preferably less than 0.1 μm; commonly the surface area of fine particle size filler will be 40 to 300 m²/g. It may be for example any form of silica including comminuted forms of crystalline silicas including for example sand, but is preferably a colloidal form for example a pyrogenic or fumed silica, or a precipitated silica. The fine particle filler may also be for example titanium dioxide, aluminium oxide or a radio-opaque filler and mixtures thereof.

The mixture also contains large particle size filler (LF) having a mean size value in the longest dimension of 0.5 μm to 80 μm, preferably less than 55 μm and most preferably less than 30 μm and desirably containing less than 5% by volume of particles having mean size value of more than 80 μm. The large particle size filler may have a smooth distribution of particle size value but may show a single peak at the mean value or that filler may comprise a mixture of fillers which may in particle size distribution show two or more, but preferably two, three or four peaks in a distribution of particle size value within the range.

The large particle size filler may also be siliceous such as for example silica in the form of fine sand and other crystalline quartz, but may also be any suitable silicate glass such as for example barium aluminium silicate, or a glass incorporating a rare earth or other suitable oxide such as lanthanum, strontium, tantalum, zirconium, gadolinium, dysprosium, hafnium, or tungsten oxide and other fillers such as alumina, titanium dioxide calcium fluoride so as to impart a desired property such as radio-opacity, refractive index and hardness. However, choice of filler may depend upon other features of the present composition such as desired colour for matching existing teeth and the type of catalyst being incorporated. It may be desirable for the composition to include a radio-opaque filler because the dentist can more easily ascertain the location and anatomic form of the composition within a cavity.

In order to assist with incorporation of the filler in the preparation of the present composition, a dispersing agent is required in particular in conjunction with the fine particle size filler. Incorporation may also be assisted by the use of a diluent e.g. methylene chloride but such a diluent will generally require subsequent removal.

A preferred dispersing agent for the fine particle size filler contains a mixture of compounds comprising a phosphorus oxyacid having the formula:

wherein $R_1$ is an organic group containing a terminal chain which is either a hydrocarbon group having at least six carbon atoms or a polyether or polyester of molecular weight greater than 200 preferably from 500–10,000, $R_2$ is either a group as specified for $R_1$, a hydrogen atom, or a hydrocarbyl or substituted hydrocarbyl group not having a terminal chain of at least six carbon atoms and an organic base nitrogen compound having the formula:

wherein $Z_1$ is a group as specified for $R_1$ above and $Z_2$ and $Z_3$ which may be the same or different are as specified for $R_2$ above.

The molar proportion of acids to bases in the above dispersing agent may be from 0.5:1 to 100:1 but it is better to have an approximately 50% molar excess of acid present and therefore preferred proportions are from 1:1 to 3:1 measured as molar ratios of acid to base.

The weight concentration of the dispersing agent in the composition of this invention is not critical but should be related mainly to the weight of the filler mixture present in the composition. The concentration of acid and amine in the composition should generally be in the range separately 0.1% to 5% by weight relative to weight of filler mixture. For best results a concentration of less than 10% by weight of the dispersing agent is preferred.

Dispersions of fine particle size filler in organic media including a dispersing agent based on the above acids and amines is described in European Patent Application No. 13491-A1, the disclosure of which is included herein by way of reference.

It is desirable, particularly at higher levels of filler loading to use a dispersing agent in conjunction with inclusion of large particle size filler. The dispersing agent assists in maintaining fluidity of the composition. Preferred dispersant for the large particle size filler are polymeric dispersants such as those described in British patent specification No. 1493393, the disclosure of which is incorporated herein by way of reference. The amount of such dispersant to be used varies widely depending upon for example the chemical structure of the dispersant, the type and particle size of the filler and the polymerisable material.

The particle size of the large particle size filler may if desired be reduced before incorporation with the other ingredients to form the present composition, by for example dry milling. The filler so milled or as supplied may then be pre-mixed with any dispersant and some of the other ingredients of the composition before all the components of the composition are finally mixed.

The dental compositions of the present invention include free radical generating systems. These include those based on a catalyst such as for example organic peroxide and an accelerator such as an organic amine as described in some of the afore-mentioned specifications. Also included are those catalyst systems which are sensitive to ultra violet radiation such as those based on monoketones, hydroxy ketones and their alkyl esters. Preferably the catalyst is activated by visible light for example those described in British patent specification No. 1408265 and Belgian Pat. No. 789950, the disclosures of which are incorporated herein by way of reference. These catalysts comprise a photo sensitiser and a reducing agent capable of reducing the photosensitiser when the latter is in an excited state.

The dental compositions of the present invention may depending upon the catalyst incorporated therefor be cured for example by irradiating the compositions with ultra violet radiation, that is, with radiation having a wavelength in the range about 230 mμ up to 400 mμ. The compositions may also be, and preferably are, cured by irradiating with visible radiation having a wavelength in the range 400 mμ to 500 mμ. Alternatively, a mixture of ultra violet and visible radiation may be used.

Suitably the concentration of the photosensitiser is 0.001% to 10% by weight, preferably 0.1% to 5% by weight and the concentration of reducing agent is similar but preferably is 0.25% to 5% by weight, most preferably 0.25% to 1.00% by weight, all these percentages being by weight of the polymerisable material in the dental composition.

A preferred photosensitiser is selected from fluorenone, substituted derivatives thereof, and α-diketones having the structure:

in which the groups A, which may be the same or different, are hydrocarbyl groups or substituted hydrocarbyl groups including camphorquinone.

Preferred reducing agents are selected from those having the structure R₃N where the units R, which may be the same or different, are hydrogen atoms, hydrocarbyl groups, substituted hydrocarbyl groups or groups in which two units together with the nitrogen atom form a cyclic ring system, no more than two of the units R being hydrogen atoms and, where the nitrogen atom is attached directly to an aromatic group R, at least one of the other units R has a In order that a dental filling composition may be produced in which the siliceous filler in the composition adheres particularly well to the polymerisable material it is much preferred that the filler be treated with a coupling agent which is capable of reacting with both the siliceous particles and the polymerisable material before the mixing of the filler and polymiserable material is effected. The coupling agent should have the effect of increasing the strength of the bond between the filler and the cured polymerisable material in the filling.

Suitable coupling agents especially for use with glass or silica include silanes, e.g. γ-methacryloxypropyltrimethoxysilane, γ-aminopropyltriethoxysilane and γ-glycidoxypropyltrimethoxysilane.

Mixing of the polymerisable material with the filler and other ingredients to form the present dental filling composition may be effected by simply stirring the ingredients together. However as the polymerisable material optionally including copolymerisable monomer may be viscous and thus difficult to stir with the filler so as to achieve adequate mixing, the polymerisable material optionally including copolymerisable monomer may conveniently be diluted with a suitable diluent so as to reduce the viscosity thus enabling adequate mixing of the filler to be more readily achieved. When mixing has been effected the diluent may be removed, e.g. by evaporation. Suitably, the diluent may be the copolymerisable ethylenically unsaturated monomer above, the level of the other monomer subsequently being reduced to the desired extent.

However it is preferred that some of the ingredients be premixed in order to facilitate more thorough final mixing of all the ingredients. For instance the fillers are preferably separately mixed with any dispersing agent and some of the polymerisable material, and as desired in an inert diluent so that the filler is thoroughly wetted. Such a mixture incorporating a large particle size filler may be milled so as to reduce particle size of the filler before addition to the main bulk of the eventual mixture.

After mixing together all the ingredients of the present composition, any diluent which is not required for subsequent curing should be removed for example by evaporation preferably under reduced pressure so as to facilitate removal at nearer to ambient temperature and to reduce the level of air in the final mixture. Any mixing or manipulation of the mixture which includes polymerisable material and ultra violet or visible light sensitive catalyst should be carried out in substantial absence of such radiation in order to avoid premature cure. Also, where the catalyst system comprises two components such as peroxide—amine which when mixed together produce curing those two components should not be added together to the mixed bulk of the other ingredients but one such component to one half of the bulk and the other such component to the other half of the bulk.

Whilst it is primarily envisaged that the compositions of the present invention will be useful as dental filling materials, they may also be useful as dental glazes and veneers, orthodontic adhesives, denture base and for artificial teeth crowns and bridges. In particular the composition should have a stiff paste or doughy consistency if it is to be used as a filling material; it should be a liquid preferably flowable if it is to be used as a dental glaze so that it may be applied to the prepared tooth surface e.g. by brushing and thereafter flow before curing so as to produce a smooth surface. If the composition is to be used as an orthodontic adhesive, then a wide range of consistency is envisaged depending on what is to be adhered to the tooth and the way in which the adhesive is to be applied; for example where a dental bracket is to be adhered to a tooth the composition may be a liquid so that it may be applied to the tooth and the bracket pressed into the liquid film or the composition may be a dough which is applied to the back of the bracket or to a small area of the tooth surface before mating the tooth and bracket. Accordingly the present composition is coherent and not crumbly or powdery.

Where the dental composition of the present invention contains a catalyst activatable by ultraviolet or more particularly visible light, it may conveniently be packed in small containers (e.g. 10 g. capacity) or unit dose form so as to facilitate handling in the surgery and to reduce the risk of inadvertent curing by U.V. radiation or stray light. However, where the catalyst consists of two components which react when mixed as in for example peroxide—amine combinations, the present composition is preferably packed in two containers, one containing peroxide and the other the amine, together with such other components of the mixture such that when the contents of the two containers are mixed, e.g. in a dentist surgery, the present composition is produced.

For cosmetic purposes the present composition may have a flesh coloured (for dental base) or natural tooth appearance, and hence the present composition may include small quantities of pigments, opalescent agents and the like. The composition may also include small quantities of other materials such as anti-oxidants and stabilisers provided that they do not substantially affect the cure.

It is preferred that the surface of the tooth be cleaned before application of the composition. The tooth may be so cleaned by for example grinding with a rotating wheel or brush or by etching using for example aqueous phosphoric acid. For complex cavity work, etching and bevelling of enamel margins may improve retention and anatomic form of the composite restoration, particularly if used in conjunction with a bonding agent (e.g unfilled polymerisable material). The dental composition may be applied to the tooth, e.g. as a filling to a cavity in the tooth, and the polymerisable material is then polymerised so that the composition is formed into a hard material. When used as a dental filling material it is preferred that a cavity liner is first applied. The liner may be any normally used in the composite filling art such as polycarboxylate and calcium hydroxide aqueous slurry cements. Suitable lining cements are described in Journal of Dentistry, Vol 6 No. 2, 1979, pages 117–125. In general it is preferred to avoid liners such as zinc oxide—eugenol liners which may interfere with the curing of the composite.

The invention is illustrated with reference to the following Examples:

EXAMPLE 1

Condensate (35.2 g, 0.1 mole) obtained by reacting 2,2-bis-(4-hydroxyphenyl)propane and propylene oxide in a molar ratio of 1:2 (oxypropylated Bisphenol A) was dissolved in approximately 100 g of methylene dichloride and the resulting solution was added dropwise to a solution of 33.6 g (0.2 mole) of hexamethylene diisocyanate in 100 g of methylene dichloride under an atmosphere of nitrogen gas. 4 drops of dibutyl tin dilaurate (available as "Mellite"12, "Mellite" is a registered Trade Mark) were added as catalyst. The mixture was stirred under nitrogen for 1 hour after which it was heated under reflux conditions for 9 hours. The mixture was then cooled and a solution of 29 g (0.2 mole) of hydroxypropyl methacrylate in 100 g of methylene dichloride was added after which the mixture was heated under reflux conditions for 3 hours. The hydroxypropyl ester comprised isomers in weight ratio 2-hydroxypropyl (2.6 parts) to 1-methyl-2-hydroxyethyl (1 part). The mixture of vinyl urethane and methylene chloride was then cooled. Dimethyl long-chain alkyl tertiary amine (0.6 g Armour Hess Armeen DM 16D), di-(2-ethylhexyl) phosphoric acid (1.00 g.) and methacryl silane (1.33 g. Union Carbide Corporation grade A 174) were added to the mixture. Fine particle size filler (Aerosil A 130); mean size value 0.02 $\mu$m) was then stirred in amount appropriate to the level required in the final composition together with triethylene glycol dimethacrylate in weight amount the same as the vinyl urethane.

Large particle size fillers (LF) were prepared by milling in methylene chloride (50:50 by volume) which contained silane (A 174) 2% w/w on filler and water (0.2% w/w on filler). One mixture ($LF_1$) had filler mean size value 3.8 $\mu$m and the other mixture ($LF_2$) had value 2.5 $\mu$m.

To each mixture was added camphorquinone (0.75% by weight of polymerisable material) and diemthylaminoethyl methacrylate (0.5% by weight of polymerisable material). Methylene chloride was removed by stirring at ambient temperature followed by vacuum evaporation.

Samples of the resulting dispersions which were fluid plaste compositions were charged to polyethylene moulds of (1) length 2.5 mm and diameter 3 mm and (2) length 25 mm and square (2 mm side) cross-section. Curing was effected by 1 minute exposure of the total sample under test to light from the end of Quartz optic light guide length 11 cm. diameter 8 mm. coated along its length with a Netlon sleeve (trade mark) and shrink wrap coating of polyvinyl chloride. The light source was a tungsten halogen lamp 12 volt, 75 watt, (Thorn Electrical A.1/230) fitted with an ultra violet filter. Physical properties of the cured moulded samples were then determined—samples (1) for Compressive strength and Diametral Tensile Strength and samples (2) for Flexural Strength after sample immersion in deionised water at 37° for 72 hours.

|  |  | A | B | C | D | Amalgam |
|---|---|---|---|---|---|---|
| FF |  | 20 | 10 | 22 | — |  |
| $LF_1$ |  | 70 | 67 | 46 | 100 |  |
| $LF_2$ | Filler | 10 | 23 | 32 | — |  |
| VFF | by | 26.3 | 14.2 | 32.4 | — |  |
| VLF | volume | 59.1 | 59.3 | 62.9 | 64.0 |  |
| $V_{fill}$ |  | 64.3 | 61.9 | 68.5 | 64.0 |  |

| | A | B | C | D | Amalgam |
|---|---|---|---|---|---|
| Flexural Strength (MN m$^{-2}$) | 85 | 121 | 131 | 131 | |
| Diametral Tensile Strength (MN m$^{-2}$) | 37 | 45 | 53 | 50 | 47 |
| Compressive Strength (MN m$^{-2}$) | 236 | 234 | 256 | 287 | 350 |
| Wear ratio (after 501 hours) | 1.03 | 1.09 | 0.36 | 4.76 | 1.00 |

Wear strength was evaluated by the method described in J. Biomed. Mater. Res., (1975) Vol. 9 Pages 341 to 353 and are expressed as ratios compared to wear of amalgam.

The results show that the compositions of the present invention containing a mixture of particle size filler have similar physical properties to amalgam and much improved wear characteristics to compositions containing large particle size filler alone.

EXAMPLE 2

A dental composition was prepared using the same vinyl urethane as that in Example 1. A resin mixture was prepared comprising vinyl urethane (50 g) triethylene glycol dimethacrylate (50 g including 10 ppm hydroquinone), camphorquinone (0.75 g), dimethylaminoethyl methacrylate (DMAEM 1 g), ultra violet stabiliser (0.5 g; "Tinuvin" 326; Ciba-Geigy Ltd.), antioxidant (1 g; "Irganox" 1010 Ciba-Geigy Ltd.).

Figure 1:
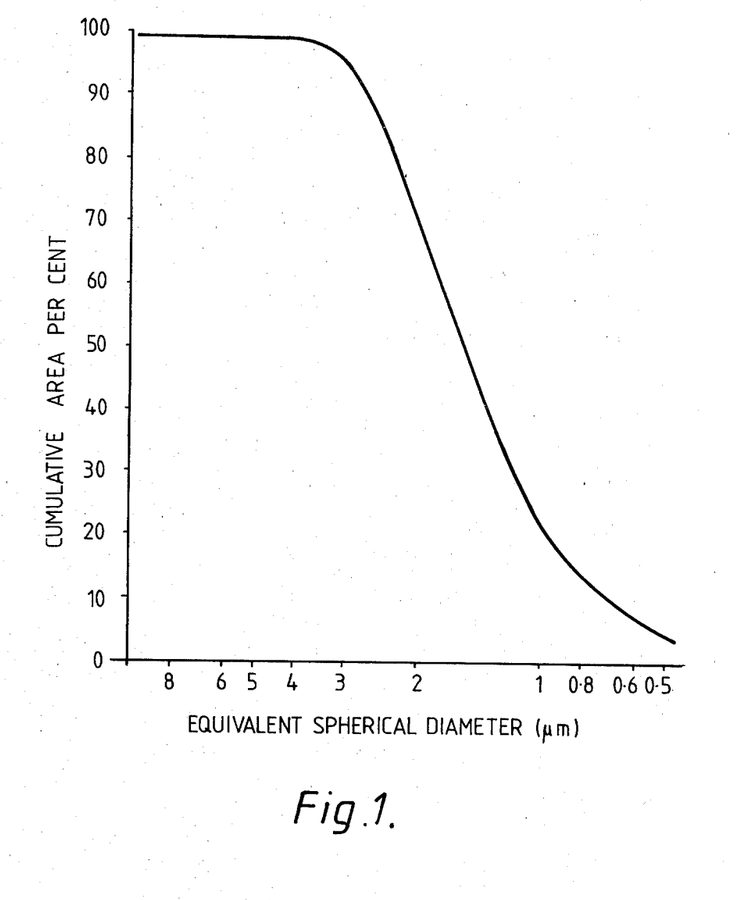

Filler A was prepared by wet milling sodium borosilicate glass, resin mixture (34% by weight of glass and resin), methacryl silane (A 174, Union Carbide Corporation, 1% w/w glass), copolymer dispersant and methylene chloride (30% by weight of the filler and resin) until the filler mean size value was 1.5 μm. Particle size distribution is shown in FIG. 1. The mixture was stirred in a dough mixer until almost all (about 97% by weight) of methylene chloride had been removed and finally milled under vacuum to reduce substantially the methylene chloride content.

Figure 2:
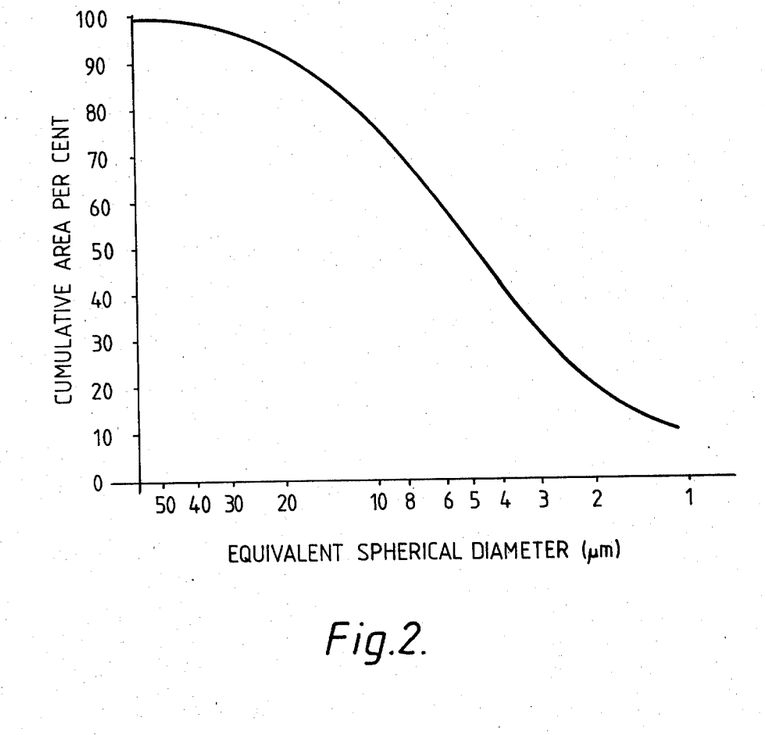

Filler B was prepared by dry milling sodium borosilicate glass until the filler mean size value was 5 μm. Particle size distribution is shown in FIG. 2. The glass was mixed with a methanol/methylene chloride/water solution (40% w/w on glass; 10/30/1 component proportion) to form a slurry. To the slurry was added methacryl silane (1% w/w on filler, Union Carbide Corporation, Grade A 174) with stirring. The glass was then filtered off and the filter cake was dried in an oven.

Filler C was prepared by mixing Aerosil OX50 (mean size value 0.02 μm), resin mixture (about 62% w/w on Aerosil and resin), methacryl silane (2.3% w/w on Aerosil; Union Carbide Corporation, Grade A 174), di(2-ethyl hexyl)phosphoric acid (DEHPA; 2.1% w/w on Aerosil), (C$_{12-14}$alkyl)dimethyl amine (Albright and Wilson Ltd., 1.2% w/w on Aerosil in a dough mixer). The resultant mixture was then milled under reduced pressure to remove the air.

A mixture was then prepared by mixing portions of resin mixture and Fillers A, B and C to product a dental composition comprising:

| | Weight (g) | Origin |
|---|---|---|
| Vinyl urethane | 8.67 | some Filler A some Filler C |
| Triethylene glycol dimethacrylate | 8.67 | most resin mixture |
| Fine Particle size filler | 7.97 | Filler C |
| Large Particle size filler | 7.74 | Filler A |
| Large Particle size filler | 65.52 | Filler B |
| Silane | 0.26 | Fillers A + C |
| DEHPA | 0.17 | Filler C |
| Amine | 0.09 | Filler C |
| Copolymer dispersant* | 0.16 | Filler A |
| Anitoxidant | 0.17 | Resin mixture |
| U.V. Stabiliser | 0.09 | Resin mixture |
| DMAEM | 0.17 | Resin mixture |
| Camphorquinone | 0.13 | Resin mixture |
| Water | 0.17 | |

*The copolymer dispersant was 95:5 weight ratio copolymer of methyl methacrylate and dimethylaminoethyl methacrylate, M 50,000 (G.P.C.).

The volume fractions of the filler were: $V_{fill}=69.6\%$ $V_{FF}=18.5\%$; $V_{LF}$ (Filler A)=17.9%; $V_{LF}$ (Filler B)=65.8%. In order to assist mixing, a small quantity of methylene chloride was added. After mixing on a dough mixer, the mixture was then milled under reduced pressure to remove air and the methylene chloride. All the mixing procedures above which involved resin in the presence of camphorquinone and DMAEM were carried out under sodium vapor discharge lamp (yellow light) so as to avoid premature cure of the resin.

Test pieces were prepared as described in Example 1 from samples of the composition and gave the following results (sample water immersion—24 hours):

| Flexural Strength | 140 MN/m$^2$ |
|---|---|
| Diametral Tensile Strength | 52 MN/m$^2$ |
| Compressive Strength | 321 MN/m$^2$ |
| Wear ratio (after 261 hours) | 0.80 |
| Knoop Hardness | 81 |

A similar composition which was radio-opaque was prepared in which barium aluminum borosilicate glass replaced on an equal volume basis all the sodium borosilicate glass in Fillers A and B above.

Particle size distribution of Filler A and B were determined by sedimentation techniques using Sedigraph 5500L (Micromeritics Limited). Specimens for examination were prepared from samples of the fillers as prepared in methylene chloride (Filler A) and methanol/methylene chloride/water (Filler B) to which further quantities of methylene chloride were added to give required translucency. Resultant distributions are given in FIGS. 1 and 2 respectively, the equivalent spherical diameter at the 50 Cumulative area percent position being taken as the filler mean size value.

For comparison a similar formulation was prepared but containing as filler only fine particle size filler C as follows:

| Vinyl urethane | 16.74 |
|---|---|
| Triethylene glycol dimethacrylate | 16.74 |
| Fine particle size filler | 62.96 |
| Silane | 1.47 |
| DEHPA | 0.84 |
| Amine | 0.74 |
| DMAEM | 0.17 |
| Camphorquinone | 0.25 |
| $V_{FF}=47.7\%$ | |

The above composition produced test pieces having

| | |
|---|---|
| Flexural Strength | 131.1 ± 10.6 MN/m² |
| Flexural Modulus | 9.24 ± 0.6 GN/m² |
| Wear ratio (100 hours) | 4 |
| Wear (100 hours) | 155.6 μm. |

EXAMPLE 3

A number of compositions were prepared using the procedure described in Example 2 but based on the following composition in order to examine a range of visible light cure catalysts.

| | Weight (g) |
|---|---|
| Vinyl urethane | 8.70 |
| Triethylene glycol dimethacrylate | 8.70 |
| Filler A | 7.80 |
| Filler B | 65.51 |
| Filler C | 8.021 |
| Silane | 0.265 |
| DEHPA | 0.107 |
| Amine | 0.094 |
| Antioxidant | 0.054 |
| U.V. Stabiliser | 0.027 |
| Water | 0.017 |
| Methacrylate acid | 0.315 (added to the resin mixture) |
| Copolymer dispersant | 0.162 |
| Catalyst - see following table | |

The volume fractions of the filler were:
$V_{fill}=69.4\%$  $V_{FF}=18.3\%$
$V_{LF}$ (Filler A) = 17.9%  $V_{LF}$ (Filler B) = 64.7%

In preparing the compositions the ketone given in the following table was added to the composition at the same stage as camphorquinone in Example 2. The ketone and amine concentrations were 0.75 and 0.5 respectively expressed % weight on vinyl urethane and triethylene glycol dimethacrylate.

| | | | | Flexural Test | |
|---|---|---|---|---|---|
| Catalyst | | Cure Time | Flexural Strength | Modulus | Length of sample cure |
| Ketone | Amine | (s) | (MN/m²) | (GN/m²) | (s) |
| camphorquinone | DMAEM | 10 | 143 ± 12 | 16.3 ± 0.7 | 30 |
| benzil | DMAEM | 100 | 110 ± 5.8 | 10.2 ± 0.6 | 120 |
| camphorquinone | N—ethyl morpholine | 20 | 123 ± 10.2 | 15.6 ± 0.9 | 30 |
| camphorquinone | C₁₂ alkyl dimethyl amine "Armeen" 12 | 35 | 127 ± 10.7 | 14.4 ± 0.7 | 60 |
| acenaphthene quinone | DMAEM | 40 | 132 ± 10.8 | 13.2 ± 0.5 | 60 |
| benzoin | DMAEM | cured on standing | | | |
| benzophenone | DMAEM | >500* | | | |

*irradiated without ultra-violet filter.

Cure time was determined by the following procedure: A 1 g sample of the composition was placed between the plattens of an oscillating rheometer of the type prescribed in British Standard 5199:1975 but modified by the provision of an aperture in the upper platten through which the composition could be exposed to the appropriate radiation needed to cure the composition. The lower platten of the rheometer was then oscillated relative to the upper platten and the oscillations were recorded automatically. The sample was allowed to equilibrate, and then the radiation was switched on. The time taken for the oscillations to cease was recorded. The results were expressed as the time taken, for a sample 2.1 mm thick to become fully cured.

EXAMPLE 4

A sample of the composition described in Example 3 but not containing light cure catalyst was divided into two parts. To one part was added

| | |
|---|---|
| Benzoyl peroxide | 0.99 |
| "Topanol" OC | 0.02 |

To the other part was added

| | |
|---|---|
| N,N—bis—(2-hydroxylethyl-p-toluidine) | 0.52 |
| "Topanol" OC (T.M. ICI Limited) | 0.02 |

The above concentrations are expressed as weight per hundred parts by weight of composition. Equal portions from each part containing the above additives were thoroughly hand mixed. The resultant mixture had a working time 3.5 m (time after mixing until significant increase in viscosity) and a setting time 5 m (time from significant increase in viscosity to setting as judged by zero oscillation on a Wilson Rheometer). Cured samples (after 24 hour water immersion) had

| | |
|---|---|
| Flexural strength | 120 ± 8.5 MN/m² |
| Flexural modulus | 15.3 ± 0.5 GN/m² | as measured according to British Standard 5199:1975 and a wear ratio of about 0.8.

EXAMPLE 5

A composition was prepared using the procedure described in Example 2 except that Bis-GMA was used in place of vinyl urethane and that the component concentrations were as follows:

| | Weight (g) |
|---|---|
| Bis-GMA ("Nupol" 46-4005) | 8.5176 |
| Triethylene glycol dimethacrylate | 8.5176 |
| Filler A | 7.8637 |
| Filler B | 66.1353 |
| Filler C | 8.1022 |
| Silane | 0.2656 |
| DEHPA | 0.1085 |
| Amine | 0.0944 |
| Copolymer dispersant | 0.1594 |
| Water | 0.0169 |
| Camphorquinone | 0.1424 |

-continued

|  | Weight (g) |
|---|---|
| DMAEM | 0.0764 |

("Nupol" - trademark, Freeman Chemicals Corporation, Port Washington, Wisconsin, U.S.A.).

The above composition had the following performance:

| Cure time | 20 s |
|---|---|
| Flexural Strength | 135.5 ± 14.9 MN/m² |
| Flexural modulus | 17.3 ± 0.73 GN/m² |
| Wear ratio | 0.8 |
| $V_{fill}$ = 70.1% | |
| $V_{FF}$ = 18.8% | |

$V_{LF}$ (Filler A) = 18.3%
$V_{LF}$ (Filler B) = 65.4%.

EXAMPLE 6

A resin mixture was prepared by mixing at ambient temperature triethylene glycol dimethacrylate (TEGDM); 100 g including 10 ppm hydroquinone), camphorquinone (0.75 g), dimethylaminoethyl methacrylate (DMAEM 0.5 g).

Large filler was that described as Filler B in Example 2 except that the filler was barium borosilicate ("Raysorb", Owens-Illinois). Fine filler mixture was prepared as described for Filler C in Example 2 except that the above resin mixture was used and DEHPA concentration was 1.35% w/w on Filler C.

A mixture was then prepared by the procedure described in Example 2 to produce a dental composition comprising:

|  | Weight (g) | Density (g/ml) | Origin |
|---|---|---|---|
| Triethylene glycol dimethacrylate | 10.77 | 1.072 | |
| Fine filler | 22.09 | 2.2 | |
| Large filler | 65.94 | 3.09 | |
| Silane | 0.517 | | Fine filler |
| DEHPA | 0.297 | | Fine filler |
| Amine | 0.253 | | Fine filler |
| DMAEM | 0.055 | | Resin |
| Camphorquinone | 0.077 | | Resin |

The volume fractions of the filler were:
$V_{fill}$ = 75.7%
$V_{FF}$ = 50.0%
$V_{LF}$ = 68.0%

The above composition had the following performance compared with amalgam ("Amalcap", Vivadent).

|  | Composition | Amalgam |
|---|---|---|
| Flexural strength (MN/m²) | 146 ± 12.8 | 75.5 ± 7.7 |
| Flexural Modulus (GN/m²) | 24.3 ± 0.49 | 33.6 ± 6.5 |
| Compressive strength (MN/m²) | 376 ± 23.6 | — |
| Wear ratio | 0.63 | 1.00 |
| Diametral tensile strength (MN/m²) | 47.1 ± 1.8 | — |

EXAMPLE 7

For comparison purposes, a composition was prepared according to the procedure of Example 6 but using the resin mixture described in Example 2 and a different filler level. The formulation was:

|  | Weight (%) |
|---|---|
| Resin mixture | 21.66 |
| Fine filler | 3.99 |
| Large filler | 74.08 |
| Camphorquinone | 0.16 |
| DMAEM | 0.11 |

The volume fractions of the filler were:

| $V_{fill}$ | 56.3% |
|---|---|
| $V_{FF}$ | 8.3% |
| $V_{LF}$ | 54.45% |

The above composition had the following performance:

| Flexural strength (MN/m²) | 121 ± 12.4 |
|---|---|
| Flexural modulus (GN/m²) | 11.9 ± 3.0 |
| Compressive strength (MN/m²) | 270 ± 13.2 |
| Diametral tensile strength (MN/m²) | 50.9 ± 5.1 |
| Wear ratio | 4 |
| Wear (100 hours) | 154.8 μm |

Physical properties on cured moulded samples in the above Examples were determined on a Howden Testing Machine—Type EU5BS as follows:

1. Flexural Strength and Flexural Modulus. After immersion in deionised water for 24 hours (except Example 1) at 37° C., the samples were dried with tissue paper and allowed to equilibrate at room temperature for 10 minutes. Rough edges on samples were carefully sanded down using emery cloth grade 0. Cross-sectional dimensions were determined on each sample using a micrometer. Three point bend test was then carried out on each sample using a 200N load cell and a cross-head speed of 1.0±0.05 mm/minute. The load at failure was recorded and flexural strength (FS) calculated according to the following formula:

$$FS = \frac{3PL}{2bd^2} \; N/mm^2$$

where
P is the load at failure (N)
L is the distance between supports (mm correct to 0.01 mm)
b is breadth of sample (mm correct to 0.01 mm)
d is depth of sample (mm correct to 0.01 mm)

Flexural modulus (FM) was calculated according to the following formula:

$$FM = \frac{P^1 L^3}{4bd^3 y} \; N/mm^2$$

where Lbd are defined above, y is the centre point deflection (mm) of the beam on the testing machine and $P^1$ is the load on the linear portion of the load deflection corresponding to the deflection y.

2. Compressive strength. After immersion in deionised water for 24 hours (except Example 1) at 37° C., the samples were dried with tissue paper and allowed to equilibrate at room temperature for 10 minutes. The diameter was measured with a micrometer; each sample was mounted in the upright position between parallel plattens of the testing machine and tested under compression until failure. The load at failure (P measure in Newtons) was recorded and compressive strength (CS) calculated according to the formula:

$$CS = \frac{P}{\pi r^2}, N/mm^2$$

where r is the radius of sample cross-section (measured in mm correct to 0.01 mm).

3. Diametral tensile strength. After immersion in deionised water for 24 hours at 37° C., samples were dried with tissue paper and allowed to equilibrate at room temperature for 10 minutes. The length and diameter of each sample was measured using a micrometer. Each sample was placed on its side between parallel plattens of the testing machine and tested under compression of 1.0±0.05 mm/min; the load at failure (T measured in Newtons) was recorded and diametral tensile strength (TS) calculated according to the formula:

$$TS = \frac{2T}{\pi DL} N/mm^2$$

where D and L are the diameter and length respectively of the sample (measured in mm correct to 0.01 mm).

In evaluating each property above, the result from 12 samples was averaged, and any value which fell more than 15% below the average was discarded. The mean of the remaining samples was recorded with a standard deviation. The tests were repeated if more than 3 samples were discarded.

What we claim is:

1. A fluid dental composition which comprises
    (a) liquid ethylenically unsaturated polymerisable resin suitable for dental applications (A)
    (b) a mixture of fillers (B) in volume fraction from 60% to 85% where volume fraction is expressed as $$\left( \frac{\text{volume } B \times 100}{\text{volume } A + \text{volume } B} \right)$$

said mixture of fillers comprising fine particle size filler and large particle size filler, the fine particle size filler being hydrophilic and having a mean size value in the longest direction of less than 0.1 μm and being present in volume fraction from 10% to 55% where volume fraction is expressed as $$\left( \frac{\text{volume fine} \times 100}{\text{volume } A + \text{volume fine}} \right),$$

and the large particle filler having mean size value in the longest dimension of 0.5 μm to 80 μm,
    (c) polymerisation catalyst for the liquid polymerisable resin, and
    (d) dispersing agent.

2. A fluid dental composition according to claim 1 in which the filler volume fraction is from 60% to 75%.

3. A fluid dental composition according to either claim 1 in which the volume fraction of fine particle size filler is from 10% to 25%.

4. A fluid dental composition according to claim 1 in which the fine particle size filler is colloidal or precipitated silica.

5. A fluid dental composition according to claim 1 in which the large particle size filler shows a single peak in distribution of particle size.

6. A fluid dental composition according to claim 1 in which the large particle size fillers shows two peaks in distribution of particle size.

7. A fluid dental composition according to claim 1 in which the liquid polymerisable material comprises at least one diacrylate or dimethacrylate ester.

8. A fluid dental composition according to claim 7 in which the liquid polymerisable material comprises a mixture of vinyl urethane and a glycol dimethacrylate.

9. A fluid dental composition according to claim 7 in which the polymerisable material comprises a mixture of Bis-GMA and a glycol dimethacrylate.

10. A fluid dental composition according to claim 1 in which two dispersing agents are included, one to assist in dispersion of the fine particle size filler and the other to assist in dispersion of the large particle size filler or fillers.

11. A fluid dental composition according to claim 1 in which the dispersing agent for the fine particle size filler comprises a mixture of at least one organic phosphorus oxy-acid and at least one organic amine.

12. A fluid dental composition according to claim 1 in which the polymerisation catalyst is activated by visible light.

13. A fluid dental composition according to claim 12 in which the visible light activated catalyst comprises at least one α-diketone and at least one organic amine capable of reducing the α-diketone when the latter is in an excited state.

14. A fluid dental composition according to claim 1 in which the catalyst comprises an organic peroxide and an organic activator for that peroxide.

15. A method for the production of a fluid dental composition as claimed in claim 1 which comprises forming dispersions of the fillers with their appropriate dispersing agents, non-polymerisable diluent and/or a portion of the polymerisable material and subsequently adding those dispersions to the bulk of the polymerisable material and removing any non-polymerisable diluent.

16. A package containing a composition according to claim 1 wherein the polymerization catalyst (c) comprises an organic peroxide catalyst and an organic activator for said peroxide catalyst, said composition being divided into two parts, one of said parts containing the peroxide catalyst and the other of said parts containing the activator, the other components (a), (b) and (c) of said composition being present in at least one of said parts.

17. A fluid dental composition which comprises
    (a) liquid ethylenically unsaturated polymerisable resin suitable for dental applications (A)
    (b) a mixture of fillers (B) in volume fraction from 60% to 85% where volume fraction is expressed as $$\left( \frac{\text{volume } B \times 100}{\text{volume } A + \text{volume } B} \right)$$

said mixture of fillers comprising fine particle size filler and large particle size filler, the fine particle size filler being hydrophilic and having a mean size value in the longest direction of less than 0.1 μm and being present in volume fraction from 10% to 55% where volume fraction is expressed as $$\left( \frac{\text{volume fine} \times 100}{\text{volume } A + \text{volume fine}} \right),$$

and the large particle filler having mean size value in the longest dimension of 0.5 μm to 80 μm,
(c) polymerisation catalyst for the liquid polymerisable resin, and
(d) dispersing agent,
where said hydrophilic fine particle size filler is colloidal or precipitated silica, the dispersing agent (d) is a mixture of at least one organic phosphorus oxy-acid and at least one organic amine, the polymerisation catalyst (c) is activated by visible light and comprises at least one α-diketone and at least one organic amine capable of reducing the α-diketone when the latter is in an excited state.

* * * * *